US006911151B1

(12) United States Patent
Müller-Kuhrt et al.

(10) Patent No.: US 6,911,151 B1
(45) Date of Patent: Jun. 28, 2005

(54) DEVICE AND METHOD FOR THE PARALLEL SEPARATION OF SUBSTANCES BY LIQUID CHROMATOGRAPHY

(75) Inventors: Lutz Müller-Kuhrt, Berlin (DE); Ralf God, Berlin (DE); Holger Gumm, Berlin (DE); Jörg Binkele, Potsdam (DE)

(73) Assignee: SEPIAtec GmbH, Potsdam (DE)

( * ) Notice: Subject to any disclaimer, the term of this patent is extended or adjusted under 35 U.S.C. 154(b) by 0 days.

(21) Appl. No.: 09/856,099

(22) PCT Filed: Nov. 22, 1999

(86) PCT No.: PCT/EP99/09747

§ 371 (c)(1),
(2), (4) Date: Nov. 28, 2001

(87) PCT Pub. No.: WO00/31528

PCT Pub. Date: Jun. 2, 2000

(30) Foreign Application Priority Data

Jun. 14, 1999  (DE) ...................................... 299 10 725 U
Nov. 20, 1999  (DE) ......................................... 198 55 001

(51) Int. Cl.$^7$ ............................................. B01D 15/08
(52) U.S. Cl. ........................ 210/656; 73/61.56; 210/87; 210/90; 210/103; 210/198.2; 210/656; 422/70
(58) Field of Search ........................... 210/87, 90, 101, 210/103, 134, 137, 143, 198.2, 635, 637, 656, 739, 741; 73/61.52, 61.55, 61.56; 422/63, 65, 70; 436/161, 164, 180

(56) References Cited

U.S. PATENT DOCUMENTS 3,847,550 A  * 11/1974  Scott et al.
3,922,223 A  * 11/1975  Burkhartsmeir .......... 210/198.2
5,198,115 A  *  3/1993  Stalling et al. ............. 210/137
6,461,515 B1 * 10/2002  Safir et al. .................. 210/656

* cited by examiner

Primary Examiner—Joseph Drodge
(74) Attorney, Agent, or Firm—Norris McLaughlin & Marcus P.A.

(57) ABSTRACT

The invention relates to a device and a method for separating substances by liquid chromatography. The aim of the invention is to provide a device and a method by which means substances can be separated by liquid chromatography under pressure and which enable parallel separation and detection of at least several samples. The device should have a compact, economical construction. To this end, the inventive device for separating substances by liquid chromatography under pressure is characterized in that at least several liquid chromatography separating lines (17) are supplied by a single delivery unit (one or two pumps), said separating lines being arranged so that they run parallel, and in that said separating lines are combined with a sample-loading system (5) and an injection system (18) in the sample introduction area and with a multi-channel detector (13), connected to an evaluation and control unit (16), in the detection area.

13 Claims, 6 Drawing Sheets

DEVICE AND METHOD FOR THE PARALLEL SEPARATION OF SUBSTANCES BY LIQUID CHROMATOGRAPHY

BACKGROUND OF THE INVENTION

The invention relates to an apparatus and to a method for the liquid chromatographic separation of substances under pressure.

So-called chromatographic separation installations are used for the preparative and analytical separation of substance mixtures. Essentially, these installations consist in each case of a conveying unit (pump), an injection system, the actual separating device (column) and a detector. The separation of mixtures of organic components is dominated at the present time by high-pressure liquid chromatography. The reasons lie essentially in the wide range of applications and in the universality, as well as in the robustness and user friendliness of the method. It is possible to separate and detect practically any mixture of organic substances by means of high-pressure liquid chromatography. Aside from the analysis of individual samples, for which it must be possible to vary the separation parameters optimally and appropriately, there is an increasing tendency in many areas to analyze and purify large series of samples under exactly the same conditions. An exact comparability of the chromatograms and an unambiguous identification of separated substances by means of the retention times in the chromatogram are frequently needed, especially for the analytical requirements. However, unavoidable differences in the way in which chromatographic columns are filled with stationary phase material, such as the height to which the columns are filled or the packing density, can however lead to different retention times, so that an exact comparability of the chromatograms is no longer given.

Until now, for analytical and preparative purposes, individual chromatographic separation installations are used for separating individual substance mixtures. The search for pharmaceutically usable natural products and the synthesis of while libraries of substances by means of combinatory chemistry, however, had led to more stringent requirements for the sample throughput in liquid chromatographic installations in recent times.

For example, as is well known, it is possible to process sample series consecutively by serial analyses or purification of samples. However, this procedure is very time consuming and leads to long periods of time between the processing of the first and last samples. It is a disadvantage that, in carrying out liquid chromatographic separations over longer periods of time, the constancy of the conditions cannot be guaranteed, since samples, column materials and solvents, for example, may change.

Therefore, in order to analyze a large number of samples by the so-called high throughput screening, it is desirable to be able to carry out a larger number of separations simultaneously. Present parallelized separation installations require a pumping device per separating equipment (column). As a rule, however, this is uneconomic. Moreover, the individual conveying lines of such multi-channel installations exhibit retention times, which deviate from one another.

High pressure chromatographic installations are known, for which, with a total of seven pumps, one column carousel with sixteen columns, four individual detectors and one fraction collector, a maximum of four samples of four samples can be processed in parallel (Laborpraxis, December 1967, pp 61–63). In addition, because of their expensive construction in comparison to the small number of samples, which can be processed, it is not possible to work economically.

A further installation is known, with which the maximum number of samples, which can be processed in parallel, also is four (Laboratory Automation News, Vol. 2, No. 2, May 1997). Four pumps operate four columns here. Substances are detected in a UV detector, which has one deuterium lamp and four flow cells, at only two wavelengths, which can be set before the analysis. The peak recognition in the detector switches four fraction collectors. In principle, essentially several high-pressure liquid chromatography setups are used in parallel here. This is disadvantageously uneconomic.

A significant increase in the number of pumping lines can be achieved, if several channels are supplied in a parallel operation by a single pump or pump system, pumping at a constant rate, and a flow distribution, specified by the user, results.

However, because of the different flow relationships in the individual columns, a simple, uncontrolled parallel connection of several separating columns, which are supplied by a single pump, leads to a flow distribution, which can be predicted only with difficulty because of the different flow conditions in the individual columns. Before it is started up, each column must be measured for its flow properties and a characteristic flow resistance value must be obtained.

Similarly to a parallel resistance network in electric technology, one would be able to expect here also, with such a characteristic value, a corresponding distribution of the volume flow. This method of adjusting the flow in parallel operation cannot be used in practice, since it does not take into consideration any changes with time, such as aging and blocking processed in the column material.

In the DE 115 45 423 A1, an apparatus is described, with which up to 72 parallel separations are said to be possible. The apparatus is based on two circular and disk-shaped separating phases, which are connected with one another. The flow of the mobile phase is reversed in the case of this apparatus. For parallel measurements, the disks are to be provided with impermeable partitions. The detection is to be accomplished in a multi-channel detector, the details of which are not described. The separation phase is supplied by two pumps and a valve tree with mobile phase and samples. This apparatus has two critical points:

There is no detailed description of how the flows in the different channels are to be controlled when the separating columns are operated in parallel. For example, if one channel becomes blocked in the apparatus shown, the flow in the other channels, in the absence of a control system, would increase.

Likewise, it is doubtful whether the partitions on the disks prove to be tight at higher pressures. Mixing of different samples can therefore not be excluded here.

SUMMARY OF THE INVENTION

It is an object of the invention to offer an apparatus and a method for the liquid chromatographic separation under pressure, with which a parallel separation and detection, as well as a purification, if required, of at least several samples is possible, the apparatus having a compact, cost-saving construction.

This objective is accomplished with the characterizing portions of claims 1 and 6.

Advantageous further developments are given in the dependent claims.

The invention has several advantages. Significantly more samples can be separated, analyzed and purified in parallel per unit time, In the same time, in which a conventional high pressure, liquid chromatographic installation can separate only one sample or one of the above-described parallel chromatographic devices can separate four samples, the inventive equipment can separate, analyze and purify five or significantly more samples. Advantageously, in the case of the inventive apparatus, each separating line, including the separating columns, is separated physically from the others, so that mixing of the samples cannot take place. For an operation with a low pressure gradient, only one pump is required even for a parallel operation with significantly more than five separating columns or for the high pressure gradient, a maximum of two pumps are required and, for the operation of the solid phase extraction unit, also only two pumps are required. This saves space and reduces costs. Since multi-way valve are connected in parallel for the sample injection, only one valve-control system is required. Such a parallel chromatographic apparatus, operating in parallel, can advantageously be equipped with a single multi-channel detector, instead of many individual detectors. Finally, the chromatograms of the individual separating lines are absolutely comparable with one another by the installation of a flow control system, which can be calibrated.

BRIEF DESCRIPTION OF THE DRAWINGS

The invention is described in greater detail by means of examples and of drawings, in which.

Figure 1A:
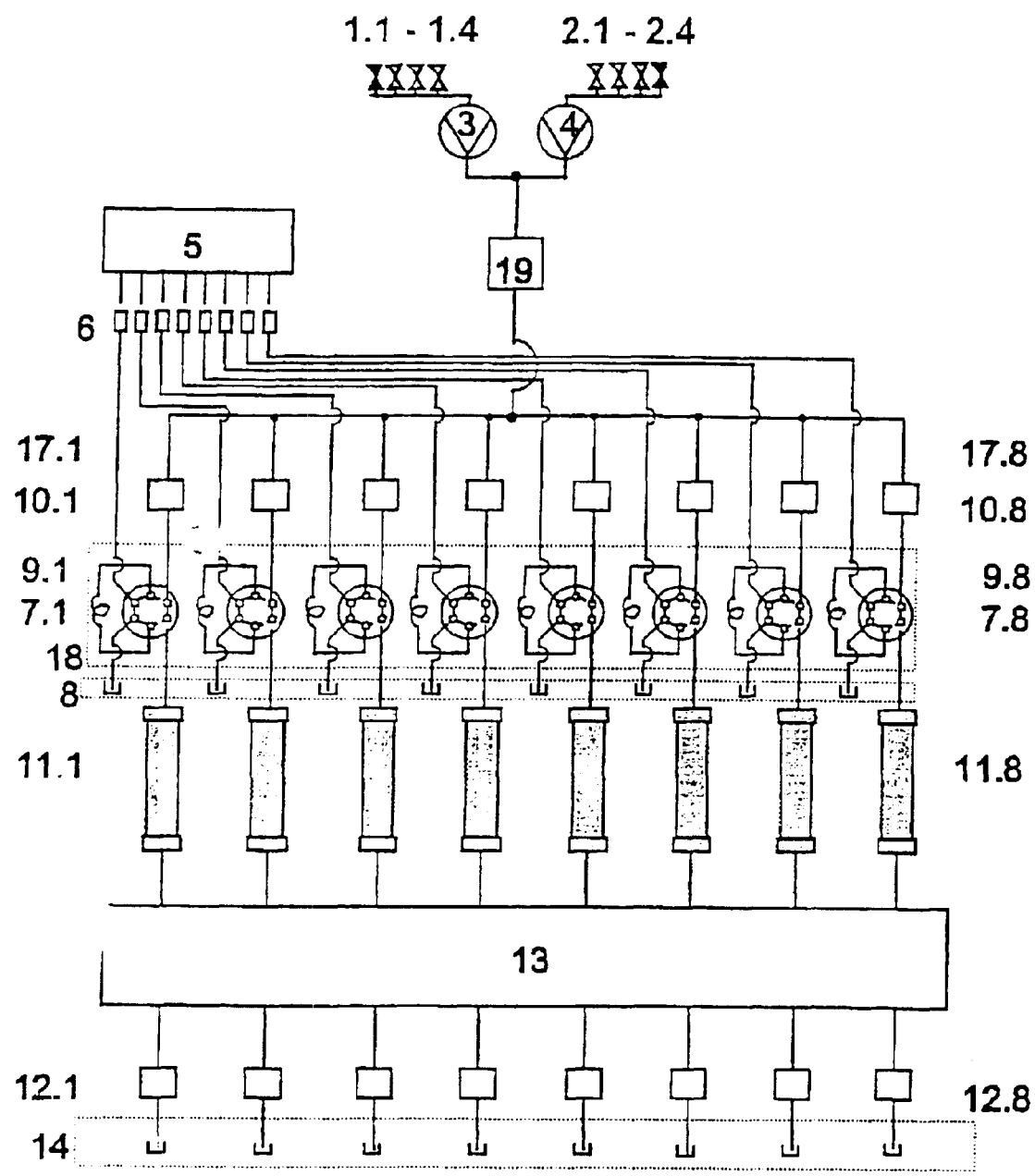
FIG. 1A shows a flow diagram with eight separating lines, as well as one variation of the flow control unit.
Figure 1B:
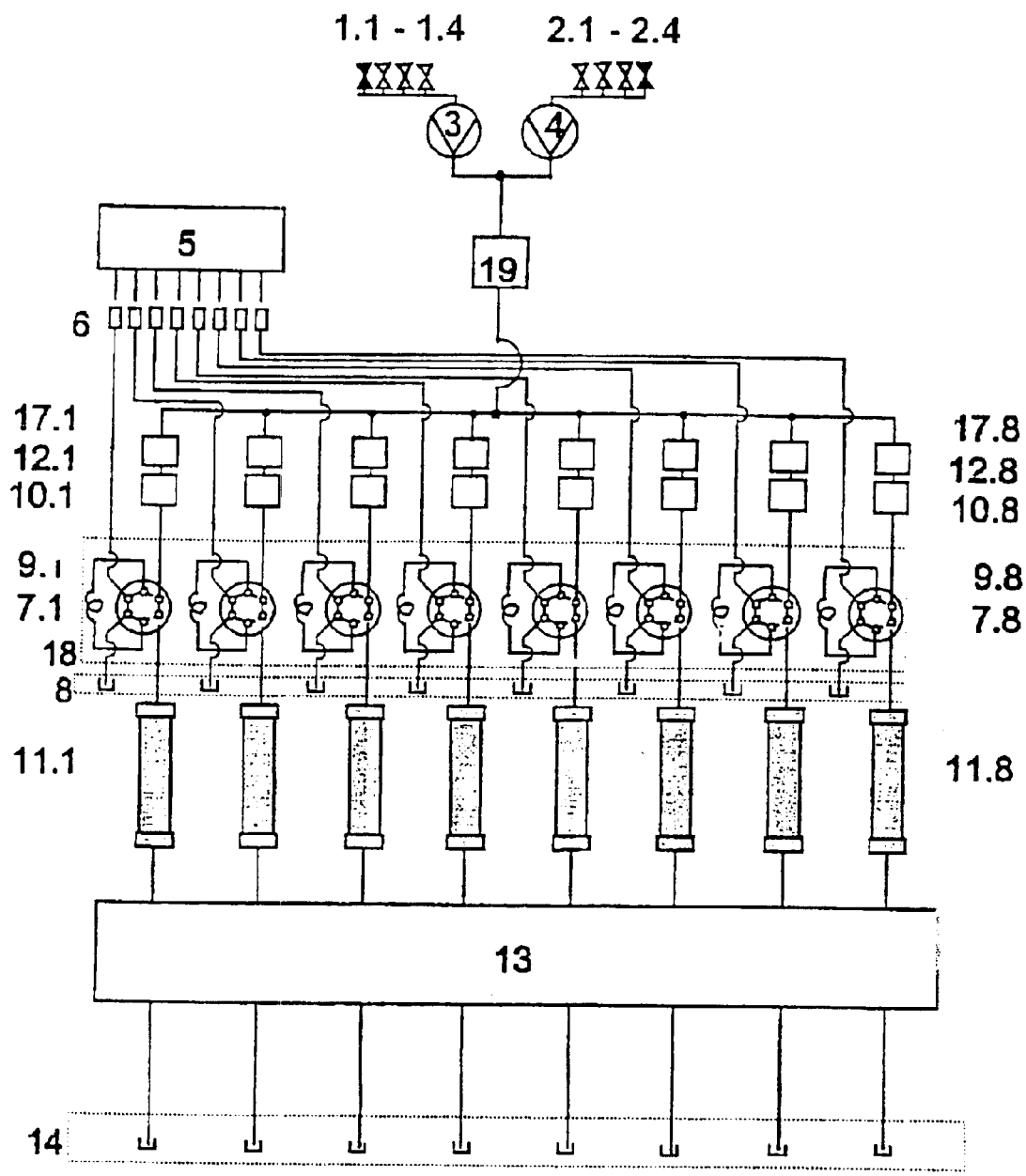
FIG. 1B shows a flow diagram with a further variation of the flow control unit.

The samples, which are to be separated, are in sample vessels. Pursuant to a preferred embodiment of the invention, these are, for example, microtiter plates 15 in FIG. 3. By means of a multi-parallel sample holding system 5, which may be constructed, for example, as an autosampler, eight samples are taken up simultaneously and supplied to the injection system 18, which consists of injection ports 6, injection valves 9 and sample loops 7 (FIGS. 1A, 1B). Through appropriate adjustment of the injection valve 9, excess sample material reaches the sample waste collector 8. If all eight sample delivery loops 7.1 to 7.8 are filled, all injection valves 9.1 to 9.8 are switched simultaneously and, in this manner, the sample loops 7.1 to 7.8, which are filled with samples, are connected with the separating columns 11.1 to 11.8, so that the samples are added in parallel and simultaneously to the separating columns 11.1 to 11.8. The separating columns 11.1 to 11.8 are disposed compactly in a separating column battery 11.

Over valves 1.1 to 1.4 and 2.1 to 2.4 and the pumps 3 and 4, the mobile phase is pumped over a pressure sensor 19, which is part of the flow control unit, into the individual separating lines 17.1 to 17.8. A low pressure gradient, as well as a high pressure gradient can be employed. In the case of the low pressure variant, the gradient is produced in a mixing chamber and pumped with a single pump. In the case of the high pressure gradient operation (FIG. 3), the mobile phase is brought together by means of two pumps 3 and 4 on the high pressure side. The mobile phase, pumped by pumps 3 and/or 4, flows over the distribution 20 to the flow regulator 10 and transports the sample, in accordance with FIG. 1A, from the sample delivery loops 7 to the respective separating column 11. The components of the samples are separated in the known manner on separating columns 11.1 to 11.8.

DESCRIPTION OF THE PREFERRED EMBODIMENT

After the separation, the components are supplied to a multi-channel detector 13. The multi-channel detector 13 may be based on the principle of known detection methods, such as ultraviolet absorption, fluorescence spectroscopy, light scattering detection or mass detection. The multi-channel detector 13 records a separate chromatogram or spectrum for each of the eight samples.

If the inventive equipment is used exclusively for analytical determinations, the sample residues and the mobile phase are subsequently transferred to a waste collector 14.

In the case of a preparative or semi-preparative operating mode, the samples are collected after the separation and processed further. Instead of the waste collector 14, a multi-parallel fraction collector 24 is then installed. In this case, a non-destructive detector, such as a multi-parallel ultraviolet absorption detector 13 with peak recognition, controls the fraction collector, which collects the purified components. A solid phase extraction unit 23 (see FIGS. 4 and 5) may be installed in front of the fraction collector 24 for purifying the fractions and transferring the fractions into an organic solvent.

Especially in the case of an analytical objective, exact comparability of the chromatograms for the unambiguous identification of separated substance by means of the retention times in the chromatogram is frequently necessary. Flow control is indispensable for this application.

The flow control unit consists of the total pressure sensor 19, the flow controller 10 and the flow meter 12. In FIG. 1A, flow controllers 10 are provided in front of the injection valve 9 in each parallel separating line 17.1 to 17.8. Flow meters 12 are disposed here, for example, after the detector 13. The necessary total pressure meter 19 is located between the pumps 3, 4 and the distribution 20 to the individual separating lines.

In FIG. 1B, a different arrangement is provided, by way of example, in which the parts of flow regulator 10 and flow meter 12 of the flow control unit are inserted compactly before the injection valve 9.

An identical flow in all separating columns 11.1 to 11.8 does not, however, guarantee the similarity of chromatograms of the same samples. Slight differences in the way in which the separating columns 11.1 to 11.8 are filled with the stationary phase material, which are attributable, for example, to columns filled to a different height or packed to a different density, can lead to different retention times for one and the same substance. Since the flows in the individual parallel separating lines 17.1 to 17.8 can be controlled individually, they can be adjusted advantageously and pursuant to the invention, so that the slight differences in the separating columns 11.1 to 11.8 are equalized. The adjustment is made by adding a calibrating component to all separating columns 11.1 to 11.8. The different retention times are measured by one detector. After the retention times are measured, the flow for the individual separating lines 17.1 to 17.8 is calculated and adjusted, so that the same retention times result in all the separating lines 17.1 to 17.8 for the calibration component.

The two methods for adjusting a flow, required for equalizing retention times and calculated in advance, are described in greater detail in the following.

Method 1 (with pressure-controlled pumping unit)

The flow meters 12.1 to 12.8 determine the actual volume flow for each separating line 17. The flow controller 10 compares this actual value with a nominal value, specified by the evaluating and control unit 16, and, with the calculated control difference, directly controls the required volume flow for the respective separating lines 17.1 to 17.8. Aside from monitoring the specification of the nominal value, the evaluating unit 16 also monitors the controller parameters.

The procedure for adjusting the volume flows for the parallel operation of separating columns is possible when the mobile phase is supplied with pressure-controlled HPLC pumps. This supplying with mobile phase is used infrequently. The difficulty in selecting a suitable pre-pressure, which depends on the subsequent column battery, makes itself felt here.

In high pressure liquid chromatography, pumps, pumping at a constant volume, are generally used.

Method 2 (with a pumping unit controlled by the volume flow)

If the mobile phase is supplied at a constant volume flow, the latter is adjusted by a special method. The above-mentioned method permits parallel volume flows to be adjusted without mutually affecting the separating lines over the total pressure. In addition, the total volume flow is distributed here completely to the individual separating lines. The volume flow valves in the individual separating lines 17.1 to 17.8 are detected by flow meters. A total pressure meter 19 determines the pressure at the output side of the pumps 3 and 4. The ratio of the total pressure to the actual volume flow value in the respective separating line represents an actual value for the flow regulator. The flow regulator 10 (such as a controller with valve) compares this actual value with a nominal value specified by the evaluating and control unit 16 and, with the calculated control difference, indirectly controls the volume flow for the respective separating line 17.1 to 17.8. In a preferred embodiment of the invention, the volume flow is determined indirectly over the pressure drop (differential pressure) at a measurement capillary.

Figure 2:
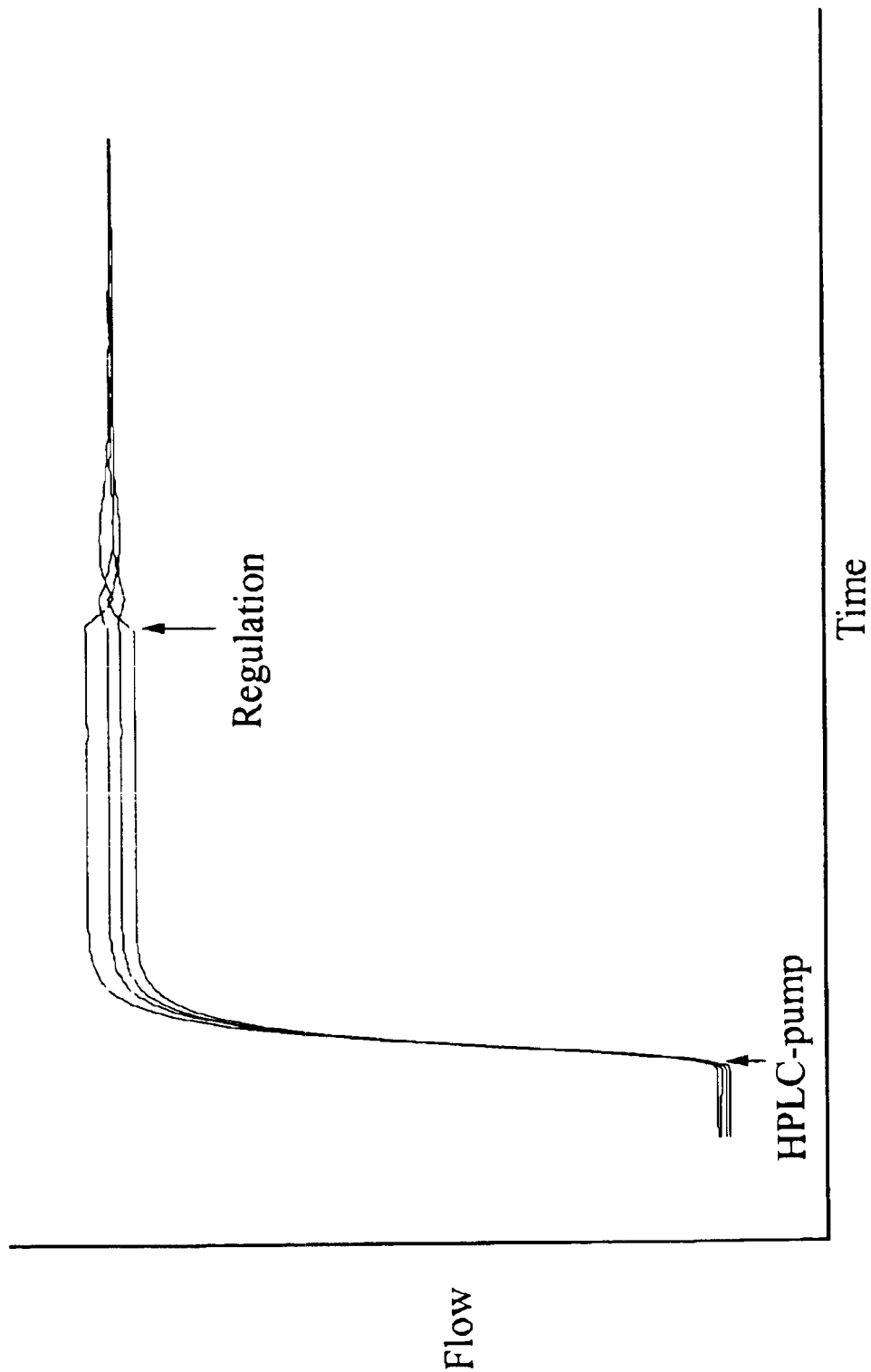
FIG. 2 shows a diagram of the mode of operation of the flow control and FIG. 3 shows a diagrammatic, perspective representation of the apparatus with 96 separating lines.

In FIG. 2, the adjusting process for four parallel HPLC separating lines 17.1 to 17.4 is illustrated in a diagram. After the HPLC pumps 3 and 4 are started, a different volume flow commences in each of the four separating lines 17.1 to 17.4. After the flow control is switched on and a common nominal value is preset, an identical volume flow exists in the separating lines 17.1 to 17.4 after a short start-up phase.

To match the retention times, a suitable standard substance is injected simultaneously into all separating lines 17 and the retention time is determined with the help of the multi-channel detector 13. From this, the evaluating and control unit 16 calculates the necessary nominal values using a special algorithm and passes these on to the flow regulating unit. The retention times of the standard substance are checked at regular intervals in order to adjust the nominal values, if necessary. Advantageously, the flow control unit also makes an error recognition possible. If the adjusted value of the flow controller in a separating line 17 deviates from a permissible range, a system error (such as a blocked column or capillary, a leak) is recognized immediately and the separating line 17 in question is disconnected. The evaluating unit 16 signals a corresponding failure report.

Figure 3:
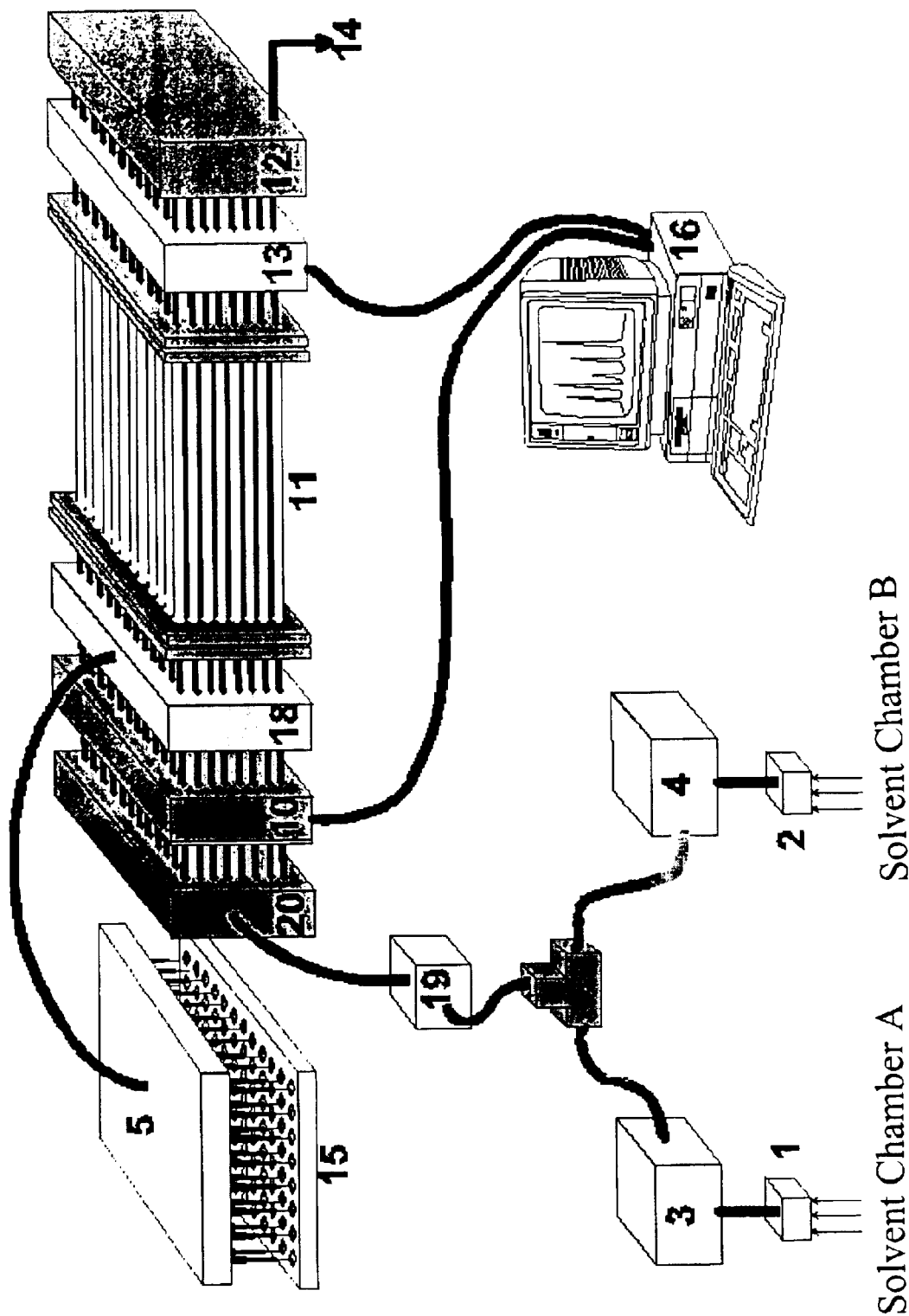

The diagrammatic representation of the apparatus, shown in perspective in FIG. 3, shows an apparatus expanded to 96 chromatographic channels. The multi-parallel sample holding system 5 can hold 96 samples simultaneously here.

Figure 4:
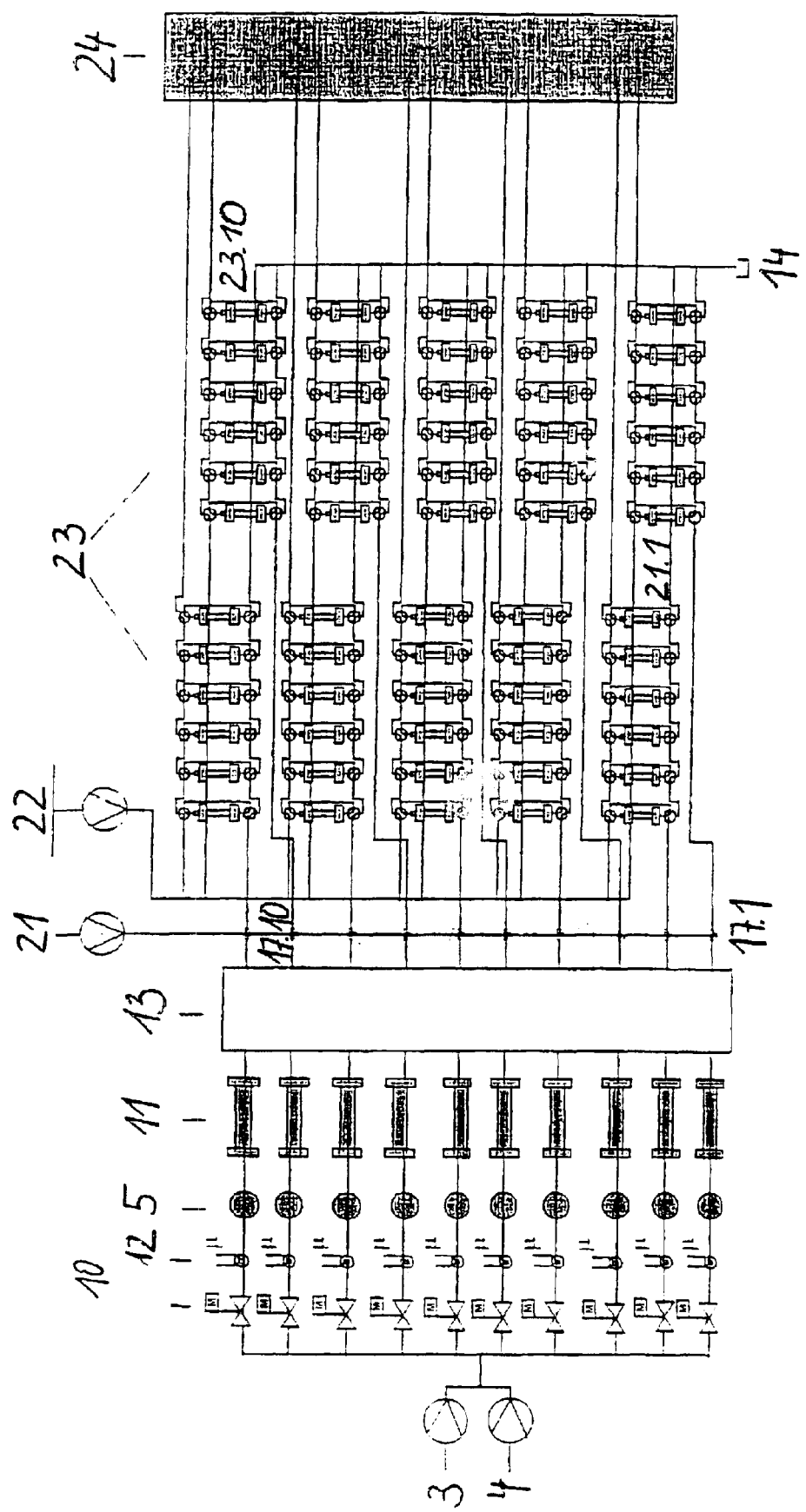
FIG. 4 shows a diagrammatic representative of the apparatus with ten solid phase extraction units, each of which has six fractionating columns
Figure 5:
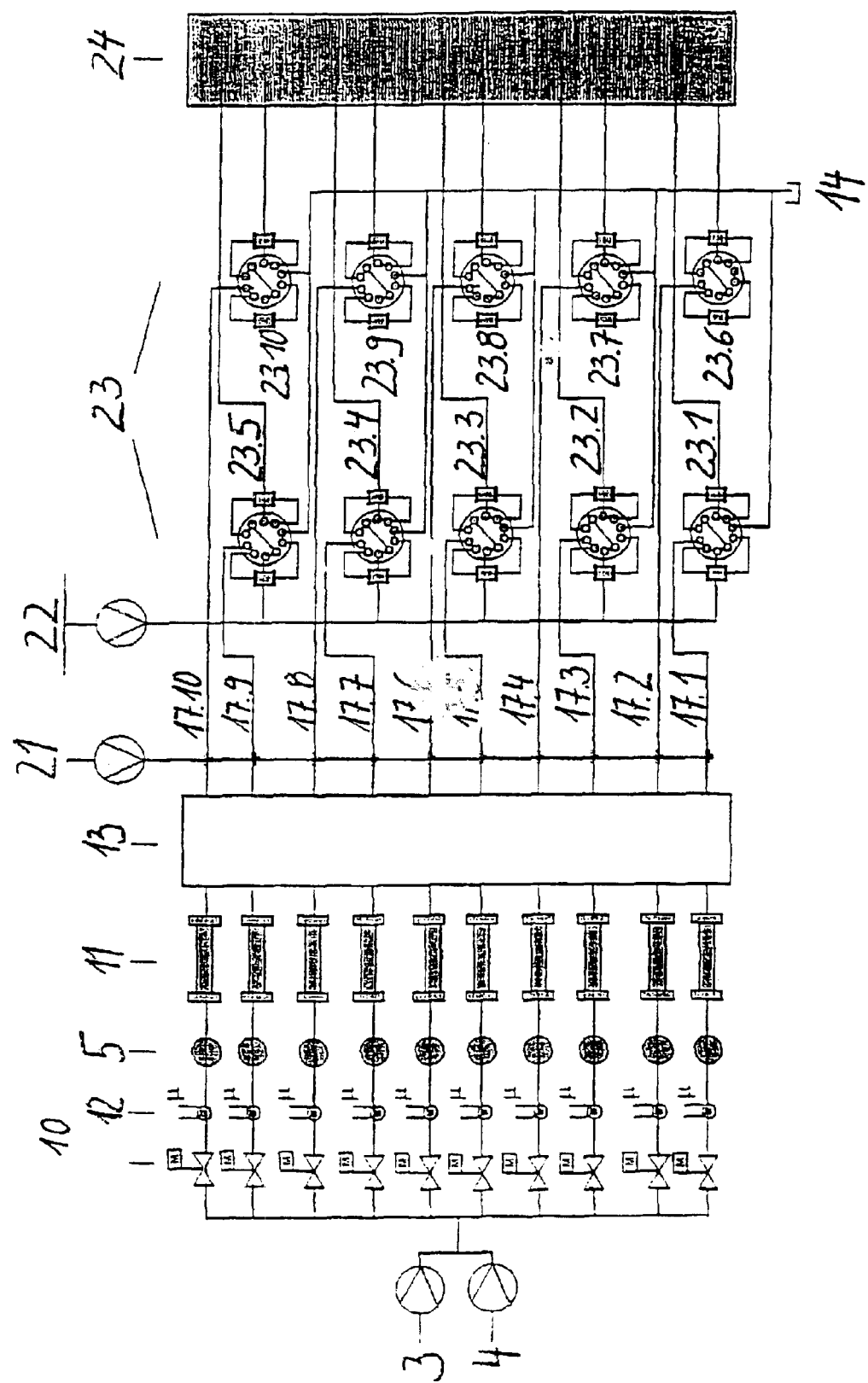
FIG. 5 shows a diagrammatic representation of the apparatus with two fractionating columns for each solid phase extraction unit.

For semi-preparative and preparative applications, a multi-parallel solid phase extraction unit 23 and a multi-parallel fraction collector of FIGS. 4 and 5 are coupled to the chromatographic channels.

According to FIG. 4, ten samples are taken up and supplied to the separating columns 11.1 to 11.10 by means of a multi-parallel sample holding system 5, which may be constructed, for example, as an autosampler. A solvent mixture is pumped over a distributor to the ten separating lines 17.1 to 17.10 shown here by means of a pump system, consisting of the pumps 3 and 4. Flow controller units, consisting of the valves 10 and the flow meters 12 and a pressure meter 19 (not shown here), as well as an appropriate computer with a flow-control program, are disposed here to ensure uniform flow in all separating lines 17.1 to 17.10. In each separating line 17.1 to 17.10, the solvent mixture is supplied over the sample holding system 5. Subsequently, the samples are passed on to the separating columns 11.1 to 11.10 to a parallel multi-channel detector 13. Water is supplied by pump 21 to all separating lines 17.1 to 17.10 in order to increase the polarity of the mixture and, with that, to make possible the extraction of the sample components on the adjoining solid phase extraction unit 23. For each separating lines 17.1 to 17.10, the solid phase extraction unit 23 contains six fractionating columns here.

In the variation of FIG. 5, two fractionating columns are provided in combination with a 10-port, two-position valve in each of the separating lines 17.1 to 17.10. The pump 22 is used to equilibrate the solid phase extraction unit 23 for cleaning the samples and finally for transferring the samples to the fraction collector 24.

LIST OF REFERENCE SYMBOLS

1.1 to 1.4 valve mobile phase supply A
2.1 to 2.4 valve mobile phase supply B
3 pump
4 pump
5 sample holding system
6 injection port
7 sample loop
7.1 to 7.8 sample loops
8 sample waste collection
9 injection valve
9.1 to 9.8 injection valves
10 flow regulator
11 battery of separating columns
11.1 to 11.10 separating columns
12 flow meter
13 detector
14 waste collector
15 microtiter plate
16 evaluation and control unit
17.1 to 17.10 separating lines
18 injection system
19 total pressure meter
20 distributor
21 pump 22 pump
23 solid phase extraction unit 23.1 to 23.10
24 fraction collector

What is claimed is:

1. An apparatus for the liquid chromatographic separation of substances under pressure, comprising
    a plurality of liquid chromatographic separating which are disposed in parallel,
    a single pumping unit in the form of one or two pumps for supplying a liquid to the separating lines
    a sample holding system for holding a plurality of samples and allowing simultaneous parallel withdrawal of the samples,
    an injection system for parallel transport of the samples from the sample holding system and a liquid from corresponding separating lines to corresponding parallel separating columns
    wherein each of the separation lines has a separate flow control unit comprising a flow controller, a total pressure meter and a flow meter, wherein the flow controller is disposed upstream of the injection system,
    a detector means connected to an evaluation and control unit for determining retention time for each of the separating columns based on data from the corresponding flow meter and total pressure meter, and
    means for independently adjusting flow via the corresponding flow controller in each of the separation lines based on the detected retention time, such that an actual retention time in all of the separating columns may be rendered the same.

2. The apparatus of claim 1, wherein the flow control unit in each of the separating lines can be controlled by software and/or hardware.

3. The apparatus of claim 1, wherein the total pressure meter is disposed on the output side of the pumping unit.

4. The apparatus of claim 1, wherein the sample holding system is connected with at least several parallel sample holding lines over at least several corresponding injection ports
    wherein the injection system comprises injection valves and sample loops which are connected with corresponding separating columns, the separating columns being coupled with the retention time detector means, the retention time detector means comprising a plurality of determination channels.

5. The apparatus of claim 1, wherein the separating columns are combined compactly into a battery of separating columns.

6. The apparatus of claim 1, wherein injection system comprises each injection valve is disposed upstream of the corresponding separating column.

7. The apparatus of claim 1, wherein injection system comprises each injection valve constructed as a multiple way valve.

8. The apparatus of claim 1, wherein each injection valve has switching means capable of directing flow to an injection port, a sample loop, the pumps, a waste collector or one of the separating columns.

9. The apparatus of claim 1, wherein each of the separating lines has a corresponding separating column and a corresponding solid phase extraction unit which extraction unit is coupled with a second set of one or two pumps.

10. The apparatus of claim 9, wherein a multiple way valve, which can be connected with the solid phase extraction unit, a multi-parallel fraction output unit or a waste collector, is disposed in an end region of the solid phase extraction unit.

11. The apparatus of claim 9, wherein each solid phase extraction units has at least two fractionating columns.

12. The apparatus of claim 9, wherein each of the solid phase extraction units has between 10 and 50 fractionating columns.

13. A method for the liquid chromatographic separation of substances under pressure, comprising the steps of, in order:
    supplying simultaneously a plurality of samples to plurality of corresponding separating columns by way of a plurality of corresponding separating lines,
    taking a calibration sample, simultaneously and in parallel, from each of the separating lines, and determining a retention time for each of the separating columns,
    calibrating each of the separating lines based on the respective determined retention time and adjusting flow in each separating line by way of a flow controller on the basis of data from a flow meter and an initial pressure meters, wherein the ratio of the total pressure to the volume flow to the respective separating line is used as actual value for indirectly controlling the volume flow, wherein the flow controller is disposed upstream of the separating columns.

* * * * *

UNITED STATES PATENT AND TRADEMARK OFFICE
CERTIFICATE OF CORRECTION

PATENT NO. : 6,911,151 B1
DATED : June 28, 2005
INVENTOR(S) : Muiler-Kuhrt et al.

It is certified that error appears in the above-identified patent and that said Letters Patent is hereby corrected as shown below:

Title page,
Item [30], Foreign Application Priority Data,
"Nov. 20, 1999 (DE)" should read -- Nov. 20, 1998 (DE) --.

Column 7,
Line 8, "liquid chromatographic separating" should read -- liquid chromatographic lines separating --.

Signed and Sealed this

Twenty-fourth Day of January, 2006

JON W. DUDAS
*Director of the United States Patent and Trademark Office*